(12) United States Patent
Muller et al.

(10) Patent No.: US 8,153,783 B2
(45) Date of Patent: *Apr. 10, 2012

(54) POLYSACCHARIDE BASED NETWORK AND METHOD FOR THE PRODUCTION THEREOF

(75) Inventors: Rolf Muller, Zurich (CH); Federico Innerebner, Zurich (CH); Paul Smith, Zurich (CH); Theo A. Tervoort, Zurich (CH)

(73) Assignee: InnoGEL AG, Huenenberg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/906,710

(22) Filed: Oct. 18, 2010

(65) Prior Publication Data

US 2011/0124777 A1    May 26, 2011

Related U.S. Application Data

(63) Continuation of application No. 10/493,684, filed as application No. PCT/CH02/00571 on Oct. 21, 2002, now Pat. No. 7,943,765.

(30) Foreign Application Priority Data

Oct. 23, 2001  (DE) .................................. 101 52 125
Mar. 28, 2002  (DE) .................................. 102 14 327

(51) Int. Cl.
C07H 1/00    (2006.01)
C07H 3/00    (2006.01)
C08B 37/00   (2006.01)
C08B 31/00   (2006.01)
C08B 33/00   (2006.01)
C08B 35/00   (2006.01)

(52) U.S. Cl. ........................................ 536/124; 536/102
(58) Field of Classification Search .................... None
See application file for complete search history.

(56) References Cited

U.S. PATENT DOCUMENTS

| | | |
|---|---|---|
| 3,344,216 A | 9/1967 | Protzman et al. |
| 3,622,677 A | 11/1971 | Short et al. |
| 4,072,535 A | 2/1978 | Short et al. |
| 4,657,770 A | 4/1987 | Slade et al. |
| 5,258,430 A | 11/1993 | Bastioli et al. |
| 5,262,458 A | 11/1993 | Bastioli et al. |
| 5,280,055 A | 1/1994 | Tomka |
| 5,281,432 A | 1/1994 | Zallie et al. |
| 5,292,782 A | 3/1994 | Bastioli et al. |
| 5,314,934 A | 5/1994 | Tomka |
| 5,334,634 A | 8/1994 | Bastiolo et al. |
| 5,360,830 A | 11/1994 | Bastioli et al. |
| 5,362,777 A | 11/1994 | Tomka |
| 5,382,611 A | 1/1995 | Stepto et al. |
| 5,384,170 A | 1/1995 | Bastioli et al. |
| 5,412,005 A | 5/1995 | Bastioli et al. |
| 5,415,827 A | 5/1995 | Tomka et al. |
| 5,427,614 A | 6/1995 | Wittwer et al. |
| 5,462,980 A | 10/1995 | Bastioli et al. |
| 5,569,692 A | 10/1996 | Bastioli et al. |
| 5,696,186 A * | 12/1997 | Videau ........................... 524/48 |
| 5,759,581 A * | 6/1998 | Baensch et al. ............... 424/489 |
| 5,801,207 A | 9/1998 | Bastioli et al. |
| 5,844,023 A | 12/1998 | Tomka |
| 5,874,486 A | 2/1999 | Bastioli et al. |
| 6,001,408 A | 12/1999 | Dudacek et al. |
| 6,117,925 A | 9/2000 | Tomka |
| 6,200,623 B1 | 3/2001 | Dudacek et al. |
| 6,277,899 B1 | 8/2001 | Bastioli et al. |
| 6,348,524 B2 | 2/2002 | Bastioli et al. |

FOREIGN PATENT DOCUMENTS

| | | |
|---|---|---|
| CA | 2343946 | 5/2000 |
| DE | 19517207 | 11/1996 |
| DE | 69124983 | 10/1997 |
| DE | 19729269 | 1/1999 |
| DE | 19729306 | 1/1999 |
| EP | 1008306 A2 * | 6/2000 |
| EP | 1258242 | 11/2002 |
| WO | 9404600 | 3/1994 |
| WO | 9428029 | 12/1994 |
| WO | 9428063 | 12/1994 |
| WO | 9504104 | 2/1995 |
| WO | 9607693 | 3/1996 |
| WO | 9631561 | 10/1996 |
| WO | 9748764 | 12/1997 |
| WO | 9806755 | 2/1998 |
| WO | 9923118 | 5/1999 |
| WO | 9933357 | 7/1999 |
| WO | 0185836 | 11/2001 |
| WO | 0238132 | 5/2002 |

OTHER PUBLICATIONS

Hoover, "Starch Retrogradation," Food Reviews International, vol. 11, No. 2 (1995), pp. 331-346.
Parovuori et al., "Effects of enzymically modified amylopectin on the rheological properties of amylose-amylopectin mixed gels," Food Hydrocollioids, vol. 11, No. 4 (1997), pp. 471-477.
Parker, et al., "Aspects of the Physical Chemistry of Starch," Journal of Cereal Science, vol. 34 (2001), pp. 1-17.
Picout et al., "Co-gelation of calcium pectinate with potato maltodextrin. Part 1. Network formation on cooling," Carbohydrate Polymers, vol. 43 (2000), pp. 133-141.
Picout et al., "Co-gelation of calcium pectinate with potato maltodextrin. Part 2. Analysis of co-gel moduli," Carbohydrate Polymers, vol. 43 (2000), pp. 143-153.
Miles et al., "The Roles of Amylose and Amylopectin in the Gelation and Retrogradation of Starch," Carbohydrate Research, vol. 135 (1985), pp. 271-281.
Leloup et al., "Microstructure of amylose gels," Carbohydrate Polymers, vol. 18 (1992), pp. 189-197.
Schwarz et al., Kunststoffverarbeitung (1997), pp. 17-19.
Powell, Engineering with Polymers (1983) pp. 49-51.

* cited by examiner

Primary Examiner — Layla Bland
(74) Attorney, Agent, or Firm — K&L Gates LLP

(57) ABSTRACT

The production of polysaccharide networks, especially starch networks, having a high network density, high solidity, a low swelling degree, and exhibiting reduced water absorption and to the uses thereof, especially, in the filed of biodegradable plastics.

13 Claims, 7 Drawing Sheets

POLYSACCHARIDE BASED NETWORK AND METHOD FOR THE PRODUCTION THEREOF

CROSS REFERENCE TO RELATED APPLICATIONS

This application is a continuation of U.S. patent application Ser. No. 10/493,684, filed Sep. 29, 2004, which is the U.S. national stage designation of International Application No. PCT/CH02/00571 filed Oct. 21, 2002, which claims priority to DE 101 52 125.1, filed on Oct. 23, 2001 and DE 102 14 327.7, filed on Mar. 28, 2002, the entire contents of which are expressly incorporated herein by reference.

BACKGROUND

The invention relates to a method for the production of a polysaccharide-based network and also to the network produced thereby and its uses.

PRIOR ART

Polysaccharides, substances which grow again naturally, especially starch, offer the following advantages with regard to their use as bioplastics: low raw material costs, high raw material purity, wide availability, broad spectrum of types having characteristic properties, raw material that grows again, $CO_2$ neutrality, easy to work, good $O_2$ barrier properties. As a result of these advantages, great efforts have been made to produce usable bioplastics, for example, starch-based, especially thermoplastic-starch-based.

The production of thermoplastic starch is described in patent specifications WO 94/28029, U.S. Pat. No. 5,362,777, U.S. Pat. No. 5,382,611 and U.S. Pat. No. 5,427,614. Thermoplastic-starch-based foamed products are described in patent specifications WO 96/07693, WO 94/28063, WP 95/04104, U.S. Pat. No. 5,801,207 and U.S. Pat. No. 5,736,586, and thermoplastic-starch-based films are claimed in WO 94/04600, U.S. Pat. No. 5,415,827 and U.S. Pat. No. 5,462,980. These solutions have the common disadvantage that thermoplastic starch is brittle, has only very low breaking elongations and a limited strength, and the most serious disadvantage is that it is exceptionally water-sensitive, absorbs water from the atmosphere and dissolves in water.

As a result of these problems, thermoplastic starch has been processed with synthetic hydrophobic polymers to form blends. Corresponding solutions are described in patent specifications U.S. Pat. No. 5,360,830, U.S. Pat. No. 5,569,692, U.S. Pat. No. 5,384,170, WO 96/31561, WO 95/04104, WO 97/48764, U.S. Pat. No. 5,280,055, U.S. Pat. No. 5,314,934, U.S. Pat. No. 5,844,023, U.S. Pat. No. 6,348,524, U.S. Pat. No. 6,277,899, U.S. Pat. No. 5,874,486, U.S. Pat. No. 5,569,692, U.S. Pat. No. 5,412,005, U.S. Pat. No. 5,334,634, U.S. Pat. No. 5,292,782, U.S. Pat. No. 5,262,458 and U.S. Pat. No. 5,258,430. These solutions where the thermoplastic starch is embedded in a hydrophobic matrix have the disadvantage that only part of the product consists of starch and is biodegradable. Some solutions use synthetic biodegradable polymers such as polycaprolactone as the matrix component which, however, are significantly more expensive than starch and also have limited mechanical and thermal properties. Further solutions are concerned with the chemical modification of starch in order to reduce its hydrophilic nature. Examples are described in patent specifications WO 98/06755, WO 99/23118 and U.S. 61/179,250. A disadvantage here is that the corresponding chemical modifications are expensive, typical advantages of natural substances only apply to a limited extent and thus the products are not very competitive.

DE 19852826 A1 relates to a poly-(a-1,4-D) glucan ("PAG") having a degree of polymerisation in the range of about 40 to 300 and to thermoplastic polymer mixtures which contain at least one such PAG and a plasticiser. In this case, the PGA is plasticised with a plasticiser (e.g. glycerol) and mixed with thermoplastic starch (TPS) in an extruder.

However, after mixing with TPS, the PAG which has merely been plasticised but not dissolved is not capable of crystallising to any appreciable extent and of forming a starch network cross-linked via crystalline regions (crystallites) with advantageous properties, in which the TPS macromolecules are interlinked through the PAG crystallites.

The approaches adopted so far to obtain starch-based biodegradable plastics were only able to realise the potential of starch to a very limited extent. The corresponding products are either unsatisfactory in relation to their properties and/or too expensive for them to have penetrated the market on a fairly large scale. Thus, starch-based biodegradable plastics have so far remained niche products.

Formulation of the Problem

The object of the present invention was to produce polysaccharide-based plastics which are biodegradable in a purely physical manner, which exhibit improved mechanical properties and lower water sensitivity compared with thermoplastic starch and some other biodegradable polymers, and especially are no longer soluble in water.

DETAILED DESCRIPTION

Invention

A method for the production of a polysaccharide-based network is disclosed herein. The network is formed from a total mixture of at least one basic polysaccharide and at least one networking polysaccharide by homocrystallisation and/or heterocrystallisation. These components are prepared separately and individually. In addition, the basic polysaccharide can be plasticised or not plasticized. Specifically, the basic polysaccharide can be plasticised after adding at least one networking polysaccharide. The networking polysaccharides can be dissolved and the components can be mixed in this state after being supplied jointly to the total mixture, preferably in a molecularly disperse fashion.

In an embodiment, the method comprises the following steps in at least one process zone: a) Supplying respectively a basic polysaccharide; b) Action of respectively a first softener on the respectively basic polysaccharide; c) Transferring the respectively basic polysaccharide into respectively a first fluid wherein respectively a first mixture is formed; d) Transferring respectively a networking polysaccharide into respectively a second fluid by the action of respectively a second softener; e) Transferring the respective second fluid into a respective third fluid; f) Incorporating the respective second fluid from step d) or the respective third fluid from step e) into one of the respective first mixtures from steps a) to c); g) Combining the respective mixtures from steps a) to f) into a total mixture; h) Forming a polysaccharide network from the total mixture formed in step g), especially by homocrystallisation between the respective macromolecules of the respective at least one networking polysaccharide among one another and/or by heterocrystallation between these respective macromolecules and the respective macromolecules of the respective at least one basic polysaccharide, after steps a) to g) have been completed.

Polysaccharide networks or gels were used as the starting point to solve this object. Since with $$G_0 \sim RTN_0N_0$$

the shear modulus $G_0$ is proportional to the network density $N_0/V_0$ (R=gas constant, T=absolute temperature), it is possible to improve the strength of networks by means of a corresponding increase in the network density i.e., by means of the number of active network elements, or network linking points $N_0$ per unit volume $V_0$. Since the network elements are formed by crystallites and these have a very limited water absorbency compared with the amorphous phase, in addition to the mechanical properties, the water sensitivity is also improved at the same time by sufficiently high network densities. As a result of the water insolubility of the crystallites at room temperature and elevated temperatures, the water insolubility of the networks is also ensured at these temperatures. On the basis of this potential of polysaccharide networks, the present invention concentrates on the possibilities for maximising the network densities of polysaccharide gels on the one hand by optimising formulations, especially maximising the concentration $C_{PNM}$ of networking polysaccharides, and on the other hand by process engineering measures, especially by influencing the network formation at low softener content $W_{M0}$ by process engineering.

In relevant investigations it was found that networks can in fact be formed at astonishingly low softener contents $WM_0$ by means of suitable process measures and the forming networks can be influenced over a wide range with regard to their properties by suitable combinations of basic polysaccharides, which exhibit no, or only a very weak, tendency to network formation, and networking polysaccharides.

Especially in relation to the polysaccharide starch, it was astonishingly found that amylopectin-like macromolecules, which only form gels of very low strength after storage times of weeks at low temperatures, which re-dissolve at temperatures around 60° C., together with amylose-like macromolecules participate in the formation of strong and even high-strength gels which only re-dissolve in an aqueous medium above 120° C. Even with a fraction of only 5% amylose-like and 95% amylopectin-like macromolecules, by means of suitable process parameters and mixture conditions, it was possible to obtain networks having properties comparable to pure amylose gels, and even superior thereto in relation to certain properties such as viscosity. Transparent networks or gels were also obtained, which are thus homogeneous, i.e., single-phase, on the size scale of visible light. This is all the more astonishing in that amylopectin and amylose were so far considered to be immiscible. In contrast, mixtures could be obtained by using sufficiently high shear velocities and especially at low softener contents, while demixing could be suppressed by suitable process measures.

Since it was possible to obtain networks of mixtures of starches which crystallise by themselves but cannot form any networks, with starches such as amylopectins which neither crystallise by themselves nor can form networks, it can be assumed that as a result of the proposed method, heterocrystallisation, especially heterocrystallisation of amylopectin-like molecules with amylose-like molecules is involved in the network formation.

The proposed method can be characterised in a simplified fashion by the fact that a basic polysaccharide or a mixture of basic polysaccharides being not yet, completely or partially plasticised, having a comparatively low softener content, is mixed in a molecular dispersed fashion with at least one completely or partly dissolved networking polysaccharide or with at least one completely or partly dissolved mixture of different networking polysaccharides having a comparatively high softener content. This is an important prerequisite especially for the formation of the desired networks, especially of single-phase starch gels. Important process measures are overheating of the networking polysaccharide, subsequent supercooling before the mixing process, partial removal of softener during or after the mixing process to obtain a low softener content, and supporting the network formation by nuclei which are produced in the method or supplied to the method as foreign nucleating agents. The formation of the network structure, especially of single-phase gels, is made possible by the formulation, and by kinetic control of the gelatinisation process by means of the corresponding process parameters.

Basic Polysaccharide

Hydrocolloids such as for example any starch or any meal, any agar, any agarose, any carrageenan, any alginate, any chitosan, any pectins, as well as mixtures of various such polysaccharides and also mixture of various types of the same polysaccharide can be used as basic polysaccharide. The basic polysaccharides can be gelatinisable or not. The polysaccharides can be supplied to the method in any state, physically and/or chemically modified.

Examples of eligible basic starches or meals are those of the following origin: cereals such as maize, rice, wheat, rye, barley, millet, oats, spelt etc; roots and bulbs such as potato, sweet potato, tapioca (cassava), maranta (arrowroot), etc; pulses and seeds such as beans, peas, mungo, lotus etc. In addition, starches and meals of other origin are also eligible such as, for example, sago, yams etc. In addition, glycogen can also be used.

The polysaccharides can be modified by cultivation or genetic engineering methods such as, for example, waxy maize, waxy rice, waxy potato, high amylose maize, Indica rice, Japonica rice etc; they can have been modified by chemical methods such as, for example, by acid conversion, pyro-conversion, cross-linking, acetylation, hydroxyethylation, hydroxypropylation, phosphorylation, graft reactions, reactions with amylases etc; they can have been modified by physical methods such as, for example, by gelatinisation (partly to completely), plasticisation, inhibition etc., or they can have been modified by a combination of cultivation, genetic methods, chemical and physical methods.

Examples of modified starches are thin-boiling starches, cold-water-soluble starches, pregelatinised starches, hydroxypropylated starches, dextrins, maltodextrin, limit dextrins, oligosaccharides, cationic starches, starch ether, starches obtained by fractionation.

Of particular interest are basic polysaccharides whose amylopectin fraction has an average chain length CL of at least 20, preferably of at least 22, more preferably of at least 24, most preferably of at least 26.

Furthermore of particular interest are basic polysaccharides whose amylopectin fraction has a blue value (BV) of at least 0.10, preferably of at least 0.13, more preferably of at least 0.16, most preferably of at least 0.18.

Also of particular interest are basic polysaccharides whose amylopectin fraction has an iodine affinity (IA) in g/100 g of at least 0.4, preferably of at least 0.6, more preferably of at least 0.8, most preferably of at least 1.0.

With respect to the molecular weight $M_W$ (weight average) of basic polysaccharides, of particular interest are polysaccharides having a weight average of more than 10,000 g/mol, preferably of more than 50,000 g/mol, more preferably of more than 100,000 g/mol, most preferably of more than 500,000 g/mol.

Networking Polysaccharides

Networking polysaccharides can be polysaccharide hydrocolloids such as, for example, starches, agar, agaroses, carrageenans, alginates, chitosans. pectins and can be defined in the following ways:

1. According to a first definition, these polysaccharides can be starches or meals which can form gels under suitable conditions. Exceptions therefrom are gels such as pure amylopectin gels which require very long gelatinisation times (days to weeks) and then form only very weak gels. Networking polysaccharides can be native or they can have been have been have been physically and/or chemically modified.

1A. One group of starches which satisfy this requirement are native or modified starches having an amylose content of at least 10%, preferably of at least 20%, more preferably of at least 30%, most preferably of at least 50%. Particularly suitable, for example, are high amylose starches, especially high amylose maize starches which can have an amylose content of up to approximately 100%, pea starches having amylose contents of more than 25% or amyloses of any origin.

1B. A further group of networking polysaccharides can be obtained by chemical and/or enzymatic decomposition, especially by debranching. Amylases such as α-amylase, β-amylase, glucoamylase, α-glucosidase, exo-α-glucanase, cyclomaltodextrin, glucanotransferase, pullulunase, isoamylase, amylo-1,6-glucosidase or a combination of these amylases can be used for the enzymatic decomposition. Especially starches from the aforesaid group of starches can be used as starting materials for the decomposition. An example of chemical, non-enzymatic decomposition of starches is the hydrolysis by means of acids such as hydrochloric acid.

2. A further definition of networking polysaccharides relates to the degree of branching $Q_b$ of the networking polysaccharides, wherein the degree of branching is less than 0.01, preferably less than 0.005, more preferably less than 0.002, most preferably less than 0.001, especially less than 0.0001

3. Additionally designated as networking polysaccharides are predominantly linear polysaccharides which can crystallise after dissolution has taken place, but in the absence of further polysaccharides form not gels but dispersions of crystallites. Such polysaccharides have average degrees of polymerisation DP of typically less than 100, but in the presence of polysaccharides which can be both non-networking or also networking, can form gels by heterocrystallisation. Of interest in relation to this type of networking polysaccharide are polysaccharides having an average chain length CL or an average degree of polymerisation of at least 10, preferably of at least 20, more preferably of at least 30, most preferably of at least 50. In the case of starches, such a networking starch can, for example, be a debranched maltodextrin which cannot form any gel itself but with an amylopectin forms gels which are comparable to the amylose gels.

4. Networking polysaccharides can on the other hand also be characterised in that the macromolecules contain linear fractions wherein these linear fractions can be main or side chains having average degrees of polymerisation DP of more than 30, preferably more than 50, most preferably more than 80, especially more than 100, most especially more than 140.

5. In addition, a further group of networking starches can be obtained by fractionation of amylose-amylopectin mixtures, for example, by fractionation by means of differential alcohol precipitation, wherein the amylose and the intermediate fraction can be used as networking starch.

According to the invention, polysaccharides which satisfy at least one of conditions 1-5 are designated as networking polysaccharides. Also designated as networking polysaccharides are mixtures wherein the components and/or the mixture satisfy at least one of the above conditions.

It is noted that in certain cases, basic polysaccharide and networking polysaccharide can be identical in terms of substance since in principle, any networking polysaccharide can also be used as basic polysaccharide. Thus, the difference between basic polysaccharide and networking polysaccharide is not of a material type in all cases, rather the terms must also be defined in connection with the method. Networking polysaccharides are treated in such a way that their potential for forming networks is optimally released whereas this need not be the case with basic polysaccharides without a suitable dissolution and supercooling process.

Method

1. Dissolution and Supercooling of Networking Polysaccharides

Only by suitably dissolving networking polysaccharides is their potential for forming networks released. As a result of plasticisation, as is commonly used for example in the production of thermoplastic starch, this is at most only partly ensured or at low softener concentration, very high temperatures are required which then lead to severe thermal decomposition. The dissolution process of networking starches is a multistage and complex process. The dissolution process usually extends over a temperature range of a few ° C. wherein successive order structures are dissolved, until complete dissolution has taken place. The temperature range is also strongly dependent on the concentration. The dissolution process is furthermore also dependent on any mechanical stressing by shearing, whereby dissolution can take place at lower temperature, and also on the pressure, dissolution time, heating rate and the pH. It can absolutely make sense if the dissolution is not complete, i.e., residual structures are still retained which can then act as nuclei for the following network formation. However, overheating of the solution is preferred wherein a complete solution and thus standardisation is achieved. Overheating is understood as the process wherein a temperature higher than the solution temperature is applied. The nuclei effective for the network formation can then be obtained in a larger number and effectiveness by means of a defined supercooling whereby very finely structured networks with correspondingly good mechanical properties can be produced, especially single-phase gels. The various parameters of the dissolution and supercooling process are thus of central importance for the structure and properties of the gels obtained after the mixing process with basic polysaccharides. In order to influence the formation of nuclei, foreign nuclei or foreign nucleating agents can also be added. Especially high numbers of nuclei and correspondingly fine and advantageous gel structures can be obtained by applying pressure and pressure waves, for example, by ultrasound before the mixing with basic polysaccharides.

Especially effective nuclei are obtained by dissolving together with networking polysaccharides, a fraction of a polysaccharide which barely forms any gels by itself wherein during the subsequent supercooling mixed nuclei are obtained, which are of particular importance for single-phase gels. In addition, greater supercoolings and correspondingly higher numbers of nuclei can thereby be used.

Various networking polysaccharides can be dissolved together, supercooled and then mixed with basic polysaccharides. However, since different networking polysaccharides have different dissolution and nucleus formation characteristics, it is frequently logical to prepare them separately and supply them separately to the mixing process.

Since networking polysaccharides contain lipids and proteins which form complexes with the linear fractions of the networking polysaccharides and thus these linear fractions are no longer available for the network formation, in cases of higher lipid and protein fractions it is indicated that these substances are preliminarily removed by extraction. However, they can also be removed from the process by filtration after the dissolution process during the subsequent supercooling where they precipitate out from the solution.

The parameters of the dissolution and supercooling process are as follows:

1. The softener content $WM_d$ in wt. % of the networking polysaccharides in step d) and e) lies in the range 40%-99%, preferably in the range 40%-94%, more preferably in the range 40%-87%, especially in the range 40%-80%, most preferably in the range 40%-70%. Comparatively low softener contents $WM_d$ or high concentrations $C_{PN}$ of networking polysaccharides in the second fluid are important to obtain low softener contents $WM_0$ and $WM_2$ and $WM_3$, high network densities $N_0/V_0$ and thus high network strengths.

2. The pressure p during the transfer in steps d) and e) is identical to the water vapour pressure $p_W(T)$ at the respective temperature, preferably a maximum of $2 p_W(T)$, more preferably a maximum of $5P_w(T)$, especially a maximum of $10p_W(T)$, most preferably a maximum of $100 p_W(T)$. High pressures are especially important in step e) to obtain high nuclei numbers $Z_K$ in the third fluid.

3. The overheating temperature $T_{LÜ}$ is step d) is at least 80° C., preferably at least 120° C., more preferably at least 160° C., especially at least 180° C., most preferably at least 200° C. This temperature can be a maximum of up to 260° C., wherein such high temperatures can only be used for very short times. High temperatures $T_{LÜ}$ have a stabilising effect on the solution, i.e., the higher $T_{LÜ}$, the lower the temperature at which the solution still remains stable afterwards, whereby the tolerance of the method is increased. In addition, overheating with suitable process control allows high nuclei numbers $Z_K$ to be obtained during the supercooling in step e). A further possibility for stabilising the solutions can be achieved by adding nuclei stabilisers.

4. The duration $\Delta t_d$ of the transfer in step d) is a maximum of 7 min, preferably a maximum of 3 min, more preferably a maximum of 1 min, especially a maximum of 0.5 min, most preferably a maximum of 0.2 min, and the minimum duration is 5 sec. Short transfer times are especially important at high temperatures $T_{LÜ}$ in order to suppress thermal decomposition.

5. The heating rate $v_d$ during transfer in step d) is at least 1° C./min, preferably at least 10° C./min, more preferably at least 50° C./min, especially at least 100° C./min, most preferably at least 200° C./min, and the maximum heating rate is approximately 300° C./min. High heating rates are especially important at high concentrations $C_{PN}$, at high molecular weights of these polysaccharides, at high temperature $T_{LÜ}$ in step d) and to suppress thermal decomposition of networking polysaccharides.

6. The temperature $T_{L1}$ in step e) is a maximum of $0.9T_{LÜ}$, more preferably a maximum of 100° C., especially a maximum of 70° C., most preferably a maximum of 30° C. The minimum temperature is approximately 0° C. Low temperatures $T_{L1}$ are important for setting high supercoolings and for setting high nuclei numbers.

7. The duration $\Delta t_e$ of the transfer in step e) is a maximum of 7 min, preferably a maximum of 3 min, more preferably a maximum of 1 min, especially a maximum of 0.5 min, most preferably a maximum of 0.2 min, the shortest times are around 5 sec. Short times are required to obtain high supercoolings $\Delta T_{LÜ}$ and thus high nuclei numbers $Z_k$ without any network formation or crystallisation of the networking polysaccharide being initiated.

8. The cooling rate $v_e$ during transfer in step e) is at least 5° C./min, preferably at least 30° C./min, more preferably at least 70° C./min, especially at least 110° C./min, most preferably at least 200° C./min and the maximum cooling rate is around 300° C./min. By means of high cooling rates a high nuclei number can be achieved in the second fluid $Z_k$ without any network formation or crystallisation of networking polysaccharides being initiated.

9. The pH in steps d) and e) for starch is in the range 5-12, preferably in the range 6-12, more preferably in the range 7 to 12. An elevated pH facilitates the solubility of networking starches. If necessary, the pH of the total mixture in step g) can be adjusted to the desired value, preferably to pH6-8, by adding a salt or base.

10. The shear velocity $G_d$ in steps d) and/or e) and f) is at least 10/s, preferably at least 100/s, more preferably at least 1000/s, especially at least 10,000/s, most preferably at least 50,000/s. The maximum shear velocities are around 100,000/s. By means of high shear velocities the solubility especially of networking polysaccharides having a high molecular weight can be significantly improved in step d) and thus higher concentrations $C_{PN}$ can be processed. In step e) high shear velocities prevent premature network formation.

The various parameters of the dissolution and supercooling process are optimised in accordance with the previous specifications so as to obtain at high concentrations $C_{PN}$, high temperatures $T_{LÜ}$ and with little thermal decomposition, stable solutions which can be supercooled to low temperatures, where high nuclei numbers $Z_K$ develop, but which do not crystallise out or form networks. This is a requirement to obtain networks having high network densities and strengths after mixing with basic polysaccharides.

Networking polysaccharides treated in accordance with the above conditions 1 to 10, are then mixed with basic polysaccharides to obtain networks wherein both networking polysaccharides and basic polysaccharides make a contribution to the forming network. On the other hand, the networking polysaccharides treated in accordance with conditions 1 to 10 even without subsequent mixing already yield new types of networks or gels which are suitable for certain applications and thereby make it possible to achieve new product properties.

After a networking polysaccharide or a mixture of networking polysaccharides has been dissolved in accordance with the above conditions and supercooled if necessary, they can be mixed directly with the basic polysaccharide or however, two or a plurality of solutions are first brought together, mixed and then supplied to the basic polysaccharides. In certain cases, it is also possible to mix prepared polysaccharides into respectively different first fluids of basic polysaccharides and then combine these mixtures to form a total mixture.

2. Mixing Basic Polysaccharides with Networking Polysaccharides

A molecular disperse mixture of basic polysaccharides and networking polysaccharides is an important requirement especially to obtain single-phase gels. Such mixtures can be obtained by using shearing and high shear velocities. If a molecular disperse or almost molecular disperse mixture has been obtained, any phase separation can be limited or completely prevented by kinetic control of the process. This means corresponding control of the cooling rate wherein the single-phase thermodynamically metastable state can be frozen in.

1. The softener content $WM_1$ in wt. % in the basic polysaccharide in step c) before the supply of networking polysaccharide is 5%-90%, preferably 5%-70%, more preferably 5%-60%, especially 5%-50%, most preferably 5%-45%.

2. The average degree of branching $Q_b$ of the polysaccharide mixture in step g) is usually higher than the average degree of branching of the networking polysaccharide used as a result of the mixing with generally significantly more strongly branched basic polysaccharides, and $Q_b$ is less than 0.05, preferably less than 0.02, more preferably less than 0.006, especially less than 0.003, Most preferably less than 0.001.

3. The softener content $WM_2$ in wt. % directly after step g) is less than 80%, preferably less than 60%, more preferably less than 50%, especially less than 40%, most preferably less than 30%. The minimum softener content $WM_2$ is 10%. The shear velocity $G_g$ during mixing of the first fluid with the second fluid is at least 10/s, preferably at least 100/s, more preferably at least 1000/s, especially at least 10,000/s, most preferably at least 50,000/s. The maximum shear velocity is around 100,000/s. By means of high shear velocities preferably a molecular dispersed mixture of fluids is achieved which is a requirement for high resulting network densities $N_0/V_0$ and especially for single-phase networks. In addition, as a result of high shear velocities $G_g$ a large number of smallest possible crystallites forming the network elements is obtained.

5. In addition, the network density can be increased after network formation has taken place in the mixture by means of suitable foreign nucleating agents. The number of nuclei Z effective in the network formation is then given by $Z=Z_k+Z_N$, where $Z_k$ is the number of nuclei in the second fluid and $Z_N$ is the number of foreign nuclei.

6. The concentration $C_{PMN}$ of networking polysaccharide processed in accordance with steps d) to f) in the mixture of step g) in wt. % is 1-95%, preferably 2-70%, more preferably 3% to 50%, especially 3% to 30%, most preferably 3-25%. By using high concentrations $C_{PN}$ of networking starches in the second and third fluid, correspondingly high concentrations $C_{PMN}$ of networking polysaccharides can be obtained in the mixture after mixing with basic polysaccharides, whereby high network densities $N_0/V_0$ and thus high network strengths can be obtained.

In at least one of steps a) to g) at least one softener can be at least partly removed from the process and this is especially important in step g) since the phase separation can be suppressed by reducing the softener content while restricting the mobility of the molecules.

In order to obtain new polysaccharide networks, a second or third fluid containing networking polysaccharide is dispersed in a first fluid, preferably mixed in a molecular disperse fashion with basic polysaccharides having the softener content $WM_1$, preferably in a plasticised state (first fluid), at a temperature $T_1>T_g$. using a thermoplastic method.

The solution of the networking polysaccharide, i.e the second or third fluid at the temperature $T_{L1}$ ($T_{L1}>=T_{LM}$) and having the nuclei number $Z_K$ is metered into the basic polysaccharides in step f) at $T_1>T_g$, for example by injection into a continuously operating mixer unit, or dissolved in the first fluid, wherein $T_1$ can be higher than, the same as or in view of a high nuclei number $Z_K$ lower than $T_1$. In special cases, the softener for the basic polysaccharide can also be added after injecting the fluid containing the networking polysaccharide. By metering in the solution, the softener content of the mixture increases to $WM_2$ since $WM_1<1-C_{PN}$ is usually satisfied. If the second or third fluid is sufficiently dispersed, the stabiliser is thereby inactivated since, as a result of the mixing process, the concentration $C_{staM}$ of the stabiliser in the mixture decreases compared with the concentration $C_{sta}$ of the stabiliser in the solution but the nuclei formed previously are retained if the process is suitably controlled. By metering in further softener or by removing softener by means of outgassing technology during or after the mixing process, the mixture of the first and second or third fluid at the end of the mixing process has the softener content $WM_3$ which usually corresponds to the softener content $WM_0$ which is present during the network formation after forming.

The temperature of the mixture $T_M$, varies during the mixing process depending on the softener content and parameters specific to the method. At the end of the mixing process the mixture temperature is $T_3$. In most cases, the procedure is such that no networking takes place during the processing of the mixture because a developing network would then be damaged, i.e., before forming the temperature should not fall below or at most should only briefly fall below the temperature $T_K$, since network formation begins ($T_M>T_K$).

This can be achieved by a suitable choice of the parameters $WM_1$, $WM_2$, $WM_3$, the concentration of the dissolved networking polysaccharide $C_{PNM}$ in the mixture, by the overheating at $T_U$, the supercooling $\Delta T_{LU}$ and the nuclei stabiliser concentration $C_{Sta}$, whereby the nuclei number $Z_K$ is given, by the number $Z_N$ of foreign nuclei in the mixture and by controlling the temperatures $T_1$ and $T_M$ and the pressure during the processing. The suppression of network formation is especially important when using high concentrations $C_{PNM}$ and with moderate to high softener contents. At low softener contents the suppression of premature network formation during the processing is less problematical because the mobility of the networking polysaccharide is then severely limited.

In certain cases, however, network formation, especially a partial network formation is strived for before the final forming, e.g. when the mixture is to be formed into fibres. A partial network formation then makes it possible to achieve especially high orientations and correspondingly high fibre strengths during the gel spin method, wherein the network is straightened in step h1 and/or step h2).

Steps a) to h), or a) to h1) and a) to h2) are preferably carried out continuously, at least in part areas wherein the suitable process zone of the process space is at least one mixer and steps a) to h) take place continuously in successive sections of the at least one mixer and steps h1) and h) take place in a forming unit following the at least one mixer. The at least one mixer can be a single-screw or a double-screw or a multiple-screw or a ring extruder or a co-kneader or a static mixer or an Ystral mixer or an agitator ball mill or another process stretch which is controllable with respect to temperature, pressure and shearing.

3. Forming and Network Formation

After the networking polysaccharides have been dispersed in a first fluid, the admixtures have been mixed in and the softener content WM3 has been adjusted, the mixture has reached the temperature $T_3$, and the forming has been supplied, the network formation desired at this time begins during the subsequent controlled cooling process. The methods commonly used in plastics technology can be used for the forming.

At low softener contents which are especially required to produce high-strength polysaccharide gels, the mobility of the networking polysaccharide is so very limited that the network formation can no longer take place or only to a very small extent during the cooling process following the forming. The mixture is then in a thermodynamically metastable frozen state at room temperature and consequently the three-dimensional network is only slightly formed. By means of the nuclei resulting from the combination of overheating and supercooling in the third fluid state and by means of further foreign nucleating agents, the limit of the lowest softener content $WM_0$ at which network formation can still take place, can be reduced to lower values. Thus, by means of suitable heat treatment following the forming, mixtures having low softener contents can also form a fully developed network that is distinguished by very small crystallites which form the cross-linking points of the network at high network density and result in transparent films. The use of ultrasonic waves is advantageous to support network formation at low softener contents $WM_0$.

Of particular importance are overheating and supercooling and/or the use of foreign nucleating agents when the mixtures are formed into shaped bodies by injection moulding. The cooling times of the shaped bodies must be as short as possible for a profitable method.

High-strength gels having low softener contents $WM_0$ are almost transparent even in the swollen state because the size of the crystallites is below the wavelength of visible light and the crystallites thus cannot scatter the light. This is an indication that it has been possible to increase the network density while the crystallite size has been reduced as a result of the measures taken. Such transparent gels are described as single-phase gels. At higher softener contents larger crystallites are formed whose size is of the order of magnitude of or greater than the wavelength of visible light, which can therefore scatter the light, are thus not transparent and have a milky white shade, as can be seen with conventional gels.

Softeners

The same solvents, softeners and softener mixtures which are suitable as solvents, softeners and softener mixtures for the corresponding polysaccharides and hydrocolloid polysaccharides according to the prior art, can be used as softeners, and these are preferably selected from the following group:

Water; glycerol; glycerol ethoxylate; polyglycerols; di-, to decaglycerols; polyglycerol monoethoxylates; reactions products of glucose with ethylene oxide; glucose monoethoxylate; glucoside; butylglucoside; alpha-methylglucoside; maltose, glucotri- and higher glucopolysaccharides, mono- and oligosaccharide syrups; alcohols; polyalcohols; butanol; erythritol; pentaerythritol; triethylolpropane; trimethylolpropane; triethylpropane monoethoxylate; propanediols; butanediols; pentanediols; hexanediols; hexanetriols; polyvinyl alcohols with 3 to 20 monomer units; polyvinyl acetates completely or partly hydrolysed to polyvinyl alcohols; trihydroxymethylaminomethane; amino alcohols; fatty alcohols; amines; hydroxyalkydamine; ethylenediamine; amides; esteramides; formamide; acid amides; sulfoxides; DMSO; quaternary ammonium compounds; glycol, ethylene glycol; ethylene diglycol; ethylene triglycol; propylene glycol; propylene diglycol; propylene triglycol; neopentyl glycol; polyethylene glycols; polypropylene glycol; polyglycols; pyrrolidone; 2-pyrrolidone or 1-methyl-2-pyrrolidone; caprolactam; polycaprolactam; sorbitol; sorbitol acetate; sorbitol diacetate; sorbitol monoethoxylate; sorbitol dipropoxylate; sorbitol diethoxylate; sorbitol hexaethoxylate; salts of carboxymethyl sorbitol; aminosorbitol; maltitol; mannitol; mannitol monoacetate; mannitol monoethoxylate; xylitol; arabitol; adonitol; iditol; galactitol; allitol; acids; carboxylic acids; formic acid; acetic acid; succinic acid; succinic acid anhydride; adipinic acid; lactic acid; tartaric acid; citric acid; malic acid; hydroxybutyric acid; maleic acid; fatty acids; dimethylsulfoxide; urea; chemically modified elements of this group, especially obtained by esterification; mixtures of elements of this group.

Softeners or softener mixtures are usually supplied to the basic polysaccharides in step b) and to the networking polysaccharides in step d), additional softener can also be supplied to the method in at least one of steps a), c), e), f), g) or h). The supply of softener in step b) can be dispensed with wherein the step c) is also dispensed with and the corresponding basic polysaccharide is transferred into a fluid or plasticised in step g) at the same time as mixing to the total mixture.

If necessary, softeners can be removed from the method in at least one step, for example by outgassing techniques, especially in at least one of steps g), h), h1), and h2). This is especially important for the production of networks having a lower softener content $WM_0$.

Admixtures

1. Foreign Nucleating Agents

Foreign nucleating agents can be supplied to the process especially at low softener contents $WM_0$ in at least one of steps a) to g) in order to facilitate network formation under difficult conditions and increase the network density. They are selected from the following groups:

Nanoparticles: nanoparticles of mono-, oligo- and polysaccharides; microcrystalline cellulose; surface-treated microcrystalline cellulose; polysaccharide microcrystallites; starch microcrystallites; mineral micro- and nanocrystallites such as, for example, boron nitride, sorbitol derivatives, especially 3,4-dimethyl dibenzylidene sorbitol; titanium oxide; calcium carbonate; nanoclays; mixtures of elements of this group.

2. Nuclei Stabilisers

Nuclei stabilisers can be supplied to the mixture of networking polysaccharides in at least one of steps d) to f) in order to suppress crystallite growth especially in highly concentrated fluids of networking polysaccharide and thus to obtain a high crystallite nuclei number during supercooling which is important for network formation at low softener contents $WM_0$ after mixing with the fluid of the basic polysaccharide. Generally used as nuclei stabilisers are highly branched polysaccharides which show no gel formation or only form very weak gels after days or weeks. Examples are glycogen, amylopectin, or agaropectin. Amylopectins having a blue value of less than 0.08 and/or having an iodine affinity of less than 0.7 g/100 g are preferably used.

3. Additives

Additives can be supplied in at least one of steps a) to g) to improve the workability, to influence the network formation and to modify the product properties having fractions in wt. % of 0.01% to 10%, preferably of 0.02% to 7%, more preferably of 0.03% to 5%. Among others, additives and adjuvants which correspond to the prior art for the manufacture of thermoplastic starch, can also be used for polysaccharide networks. Additives are especially selected from the following group of substances:

Food additives, especially antioxidants and food stabilisers; glycerol derivatives; mono-, di- and triglycerides and their stearates; glycerol monostearate; polyglycerol esters, especially of edible fatty acids; mono-, di- or triglycerides of edible fatty acids; polyethylene glycols; polyethylene glycol esters, especially of edible fatty acids; lecithins; non-ionic and ionic wetting agents and tensides; emulsifiers; complexing agents; amylose complexing agents; Na-2-stearoyl lactate; aliphatic alcohols; fatty acids, especially stearic acids, aliphatic and aromatic esters; pyridine; sugar; sugar esters, especially sugar esters of edible fatty acids; fats; fatty acid esters; wax, especially vegetarian wax such as Carnauba wax, Candelilla wax, Japan wax, Ouricury wax, Myrica gale wax, jojoba wax; polyolefin wax; natural resin; shellac; chitin; collagen, casein; mono- and oligosaccharides; dextrans; proteins; peptides; polypeptides, especially plant polypeptides; cellulose, cellulose derivatives, especially hydroxypropylated cellulose; hydrocolloids, especially alginates, carrageenan, galactomannans, glucomannans; dyes; substances usable as foodstuffs; flavourings; mixtures of elements of this group.

4. Fillers

Fillers can be supplied in at least one of steps a) to g), in order to modify the properties of the material and/or to reduce the specific raw material costs per kilo. Generally eligible are fillers which are used in plastics and bioplastics technology according to the prior art, and these are especially selected from the following group:

Minerals, especially titanium dioxide, talc, clays, wood flour; lignin; fibres, especially natural fibres such as cotton, hemp fibres, flax, ramie, jute fibres; soot; glass; glass fibres; clays; native starch; inhibited starch; cross-linked starch; starch having an amylose content of more than 40%; mixtures of elements of these groups.

5. Polymers

Polymers can be added to the method in at least one of steps a) to c), f) and g) or after g) and before h) in order to obtain mixtures or blends of polysaccharide networks with these polymers whereby the properties of the networks can be modified and/or improved for certain applications. The fraction of polymers in wt. % is 5%-95%, preferably 10%-80%, more preferably 15%-75%, most preferably 20%-70%. The polysaccharide network can be present as a matrix or as a phase dispersed in the polymer matrix. Especially suitable polymers are biodegradable polymers but non-biodegradable polymers can also be considered. The polymers are preferably selected from the following group:

Homo- or copolymers of aliphatic hydroxy acids; aliphatic polyesters of dicarboxylic acids and aliphatic diols, their lactones and lactides, especially poly(epsilon-caprolactone), polyvinyl acetate, polyhydroxybutyrate, polyhydroxbutyrate valerate, polylactic acid, polyvinyl alcohols, modified with acrylates or methylacrylates or anhydrides, their copolymers with vinyl acetate, ethyloxazoline or vinylpyridine, and partly esterified; polyvinyl acetates and partly hydrolysed; ethylene/vinyl alcohol copolymers and modified forms thereof, for example with modified end groups, especially with fatty acid end groups; cellulose; cellulose acetate and cellulose nitrate; regenerated cellulose, alkyl cellulose, carboxymethyl cellulose, cellulose propionate, cellulose butyrate; ethylene/acrylic acid copolymer; polyethylene, its vinyl copolymers, polypropylene, polyether, especially polyoxymethylene, polyoxyethylene, polyoxypropylene, polyphenylene oxide; polyamide; polyacrylonitrile; polyurethane; polyester/polyurethane copolymers; polyester/polyamide copolymers; polyglycolide; hydrophilic polymers, especially polyvinyl pyrrolidone, polyoxazoline; gelatins; proteins, especially zein, gluten, casein protein; shellac; chitin; chitosan; elastomers, especially natural rubber, latex; elements of these groups which contain anhydride, especially maleic acid anhydride groups and thus can be used as phase mediators; mixtures of elements of this group.

6. Propellants

Propellants can be supplied to the method in at least one of steps a) to g) in order to obtain foamed products wherein these can be either foamed polysaccharide networks or foamed polysaccharide polymer blends. Propellants for polymer foams according to the prior art can be used as propellants, and these are preferably selected from the following group:

Physical propellants such as $CO_2$, $N_2$, n-pentane, water, water-binding materials such as fibres of ramie, flax, hemp, jute, sisal, cotton, cellulose, water-binding materials such as loam, silica gel, gels, Sephadex, zeolites; chemical propellants, especially azodicarbonide, OBSH (p,p-oxybis(benzenesulfonylhydrazide)), TSSC (p-toluolsulfonyl semicarbazide, THT (trihydrazine triazide), peroxide, sodium bicarbonate; mixtures of elements of this group.

7. Specific Admixtures

A wide range of admixtures can be considered for specific applications. These can be selected from a wide range of material or substance classes for specific applications of starch gels. It is possible to use specific admixtures which behave inertly during the method, thus for example, magnetisable particles can be admixed and aligned by magnetic fields before the network formation in order to then remain fixed in the desired orientation, or specific admixtures which change during use of the networks, after an adjustable time or under the action of a triggering factor, or specific admixtures which change during the method, triggered for example by the temperature or pressure, by the action of chemical substances, magnetic waves, electromagnetic fields and waves, especially by standing waves, by irradiation such as electron bombardment, especially by the action of laser radiation or focused waves, or specific admixtures or combinations of inert admixtures or admixtures which change during the method, which together with the said or further action possibilities or combinations of these action possibilities produce a specific three-dimensional modulation or a three-dimensional pattern of network properties, which allow network properties to be obtained within a shaped body in a position-dependent fashion so that, for example, layers or differently defined regions of network structures are formed, which especially make it possible for defined zones of network properties differing one from the other to be formed, which allow the spectrum of high or highest network densities as far as low or vanishing network densities, or most especially which make it possible for defined cavities or cavity systems to be formed so that for example, a three-dimensional image of an organ is produced, whereupon stem cells can be cultivated which gradually disappear during the shaped body as a result of controlled processes, and grow into an implantable living organ tailor-made with respect to form and immunological characteristic.

8. Special Admixtures

The viscosity of the gel can be drastically improved by special admixtures of rubber-like materials, especially hydrocolloids, since the special admixture present as a separate phase in the starch-gel matrix can take up stress peaks. The special admixtures are preferably selected from the following group:

galactomannans such as guar gum or carob bean kernel meal; pectins, especially rhamnogalacturonans and protopectins; dextrans; xanthan; zymosan; hydrocolloids from sea salt, such as alginates, agar-agar, agarose, carrageen and carrageenans; furcellaran; hydrocolloids from lichen, such as lichenin and isolichenin, or hydrocolloids as exudates from woods such as tragant (Astragulus gum), Karaya gum, gum arabicum, Kutira gum; inulin; latex; chitin; chitosan; collagen; casein; mixtures of elements of these groups.

In order to obtain optimum results, the finest possible distribution of this phase in the matrix is decisive. For the same fraction of special admixture, the viscosity gain depends decisively on its distribution in the matrix and the particle size. his is made possible on the one hand by the special admixture being pre-prepared as the finest possible powder and on the other hand, by this admixture being preliminarily swollen and then added to the basic starch in the native state with a low softener content. As a result of the shear forces acting during the mixing, the swollen soft particles of the special admixtures are fragmented and ground by the hard native starch grains so that a correspondingly finely distributed phase of the special admixture can be obtained.

The conditions for admixing the special admixtures to obtain a highly disperse phase of the special admixtures are:

A. The special admixtures have a softener content in wt. % at the time of supply of 5-90%, preferably 11-90%, more preferably 18-90%, especially 26-90%, most preferably 33-90%. Water is preferably used as a softener or swelling agent.

B. The average particle size distribution of the special admixtures with a 5% to 20% water content lies in the range 150 μm-0.1 μm, preferably in the range 100 μm-0.1 μm, more preferably in the range 50 μm-0.1 μm, especially in the range 10 μm-0.1 μm, most preferably in the range 5 μm-0.1 μm.

C. The special admixtures are added to the basic polysaccharide in the native, pregelatinised, partly or completely plasticised state in at least one of steps a) to c), preferably in step a) while the softener content of the basic polysaccharide in wt. % at this time lies in the range 1-50%, preferably in the range 1-30%, more preferably in the range 1-20%, especially in the range 1-15%, most preferably in the range 1-12%.

By means of an optimum procedure, a special admixture can be dispersed in the matrix as a highly dispersed phase wherein the average size of this phase lies in the range 50 μm-0.07 μm, preferably in the range 20 μm-0.07 μm, more preferably in the range 7 μm-1.07 μm, especially in the range 3 μm-0.07 μm, most preferably in the range 1 μm-0.07 μm.

The admixing of special admixtures under the specified conditions is also advantageous for the production of thermoplastic starch (TPS) with improved viscosity in addition to the production of impact-resistant polysaccharide networks, whereby the properties of TPS for various applications and thus their possible applications can be improved.

Structural Type of Starch Networks

By means of suitable process control it can be achieved that the forming crystallites at room temperature preferably have an A-structure. Compared with the B-structural type which is stable at room temperature, this structural type exhibits a drastically reduced water absorption for the same air humidity whereby more favourable sorption behaviour is achieved. The A structural type which is metastable at room temperature can be frozen in by kinetic control and thus also obtained at room temperature. A further possibility for obtaining the A structural type is provided by heat treatment wherein the B structural type is converted into the desired A structural type. The required temperature, which must be applied only briefly, lies above 100° C.

Parameters $T_{L0}$ Minimum temperature at which the networking polysaccharides dissolve $T_{LR}$ Recrystallisation temperature of networking polysaccharides in thermodynamic equilibrium after dissolving at $T_{L0}$ $T_{LU}$ Overheating temperature $T_{LU} > T_{L0}$ $T_{LM}$ Temperature at which the metastable state of the suppressed nuclei growth can be maintained for 10 seconds $\Delta T_{LU}$ Supercooling delta $T_{LU} = T_{LR} - T_{LM}$ $T_{L1}$ Temperature of the solution when the second or third fluid is mixed into the first fluid $T_{ML} < T_{L1} < T_{LU}$, especially $T_{ML}, <= T_{L1} < T_{LR}$ $T_1$ Temperature of the first fluid before supply of the second or third fluid $T_M$ Temperature during the mixing process $T_3$ Temperature at the end of the mixing process $T_k$ Temperature at the beginning of network formation $\Delta t_d$ Duration of transfer in step d)

$\Delta t_e$ Duration of transfer in step e)

$v_d$ Heating rate in step d)

ve Heating rate in step e)

$Z_k$ Number of nuclei in the third fluid at $T_{L1}$ $Z_N$ Number of foreign nuclei in the mixture before the first and second or third fluid Z Number of active nuclei during network formation $C_{PN}$ Concentration of networking polysaccharide in the second or third fluid $C_{pnm}$ Concentration of networking polysaccharide in the mixture $C_{sta}$ Concentration of nuclei stabiliser in the first fluid $C_{staM}$ Concentration of nuclei stabiliser in the mixture $C_N$ Concentration of foreign nucleating agent in the mixture $WM_d$ Softener content in step d)

$WM_1$ Softener content of the basic polysaccharide at the beginning of the thermoplastic method $WM_2$ Softener content of the mixture after addition of the second or third fluid $WM_3$ Softener content at the end of the mixing process $WM_0$ Softener content during network formation $W_0$ Water content during network formation $W_1$ Water content after swelling of a film with $W_0$ in water $G_d$ Shear velocity in step d)

$G_g$ Shear velocity in step g)

$p_W(T)$ Water vapour pressure at temperature T $No/V_0$ Network density after network formation has been completed DP Average degree of polymerization CL Average chain length (number of monomer units of unbranched chain segments)

$Q_b$ Average degree of branching: number of moles of branched α-glucan units/number of moles of total α-glucan units BV Blue value IA Iodine affinity [g/100 g]

$M_W$ Weightaverage of molecular weight distribution $T_g$ Glass transition temperature The softener and water contents respectively relate to the basic and networking polysaccharides, i.e., to saccharides which are constituent components of the network. A network containing, for example, 10 g basic starch, 3 g networking starch, 11 g water, 2 g glycerol, 7 g sugar and 5 g of an admixture thus has a softener content $WM_0$ of 100*(11+2)/(11+2+10+3)=50% and a water content of 100*11/(11+10+3)=45.8%.

EXAMPLES

Further advantages, features and possible applications of the invention are obtained from the following description of examples which are not to be regarded as restrictive in connection with the production of polysaccharide-based networks and their blends according to the invention.

PROPERTIES

Example 1

Figure 1:
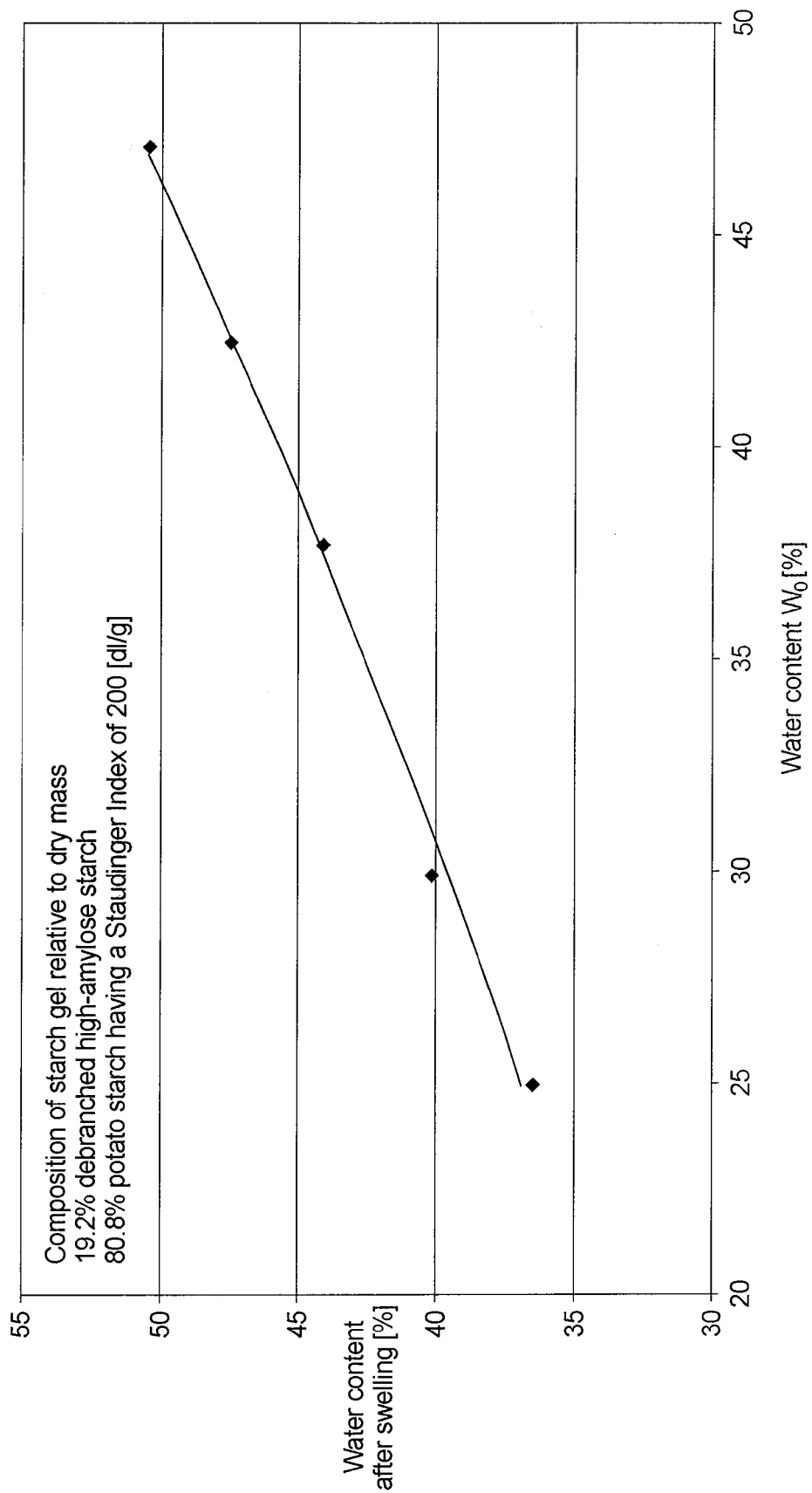
FIG. 1: shows the swelling behaviour of starch gel as a function of the water content $W_0$

FIG. 1 shows the swelling behaviour of starch gel as a function of the water content W0. The corresponding starch gel was produced with the water content W0 wherein no further softeners were used. Plasticised potato starch was used as the basic starch and debranched high-amylose starch was used as the networking starch. After production of the network, the water content $W_0$ was kept constant. The water content of a film of the network after swelling (24 hours in water) was determined using starch gel having this water content $W_0$. The profile of the curve shows that the water content after swelling decreases significantly with the water content $W_0$, i.e., the production of a gel having the lowest possible water content $W_0$ is decisive for obtaining starch gel having reduced water absorption.

Example 2

Figure 2:
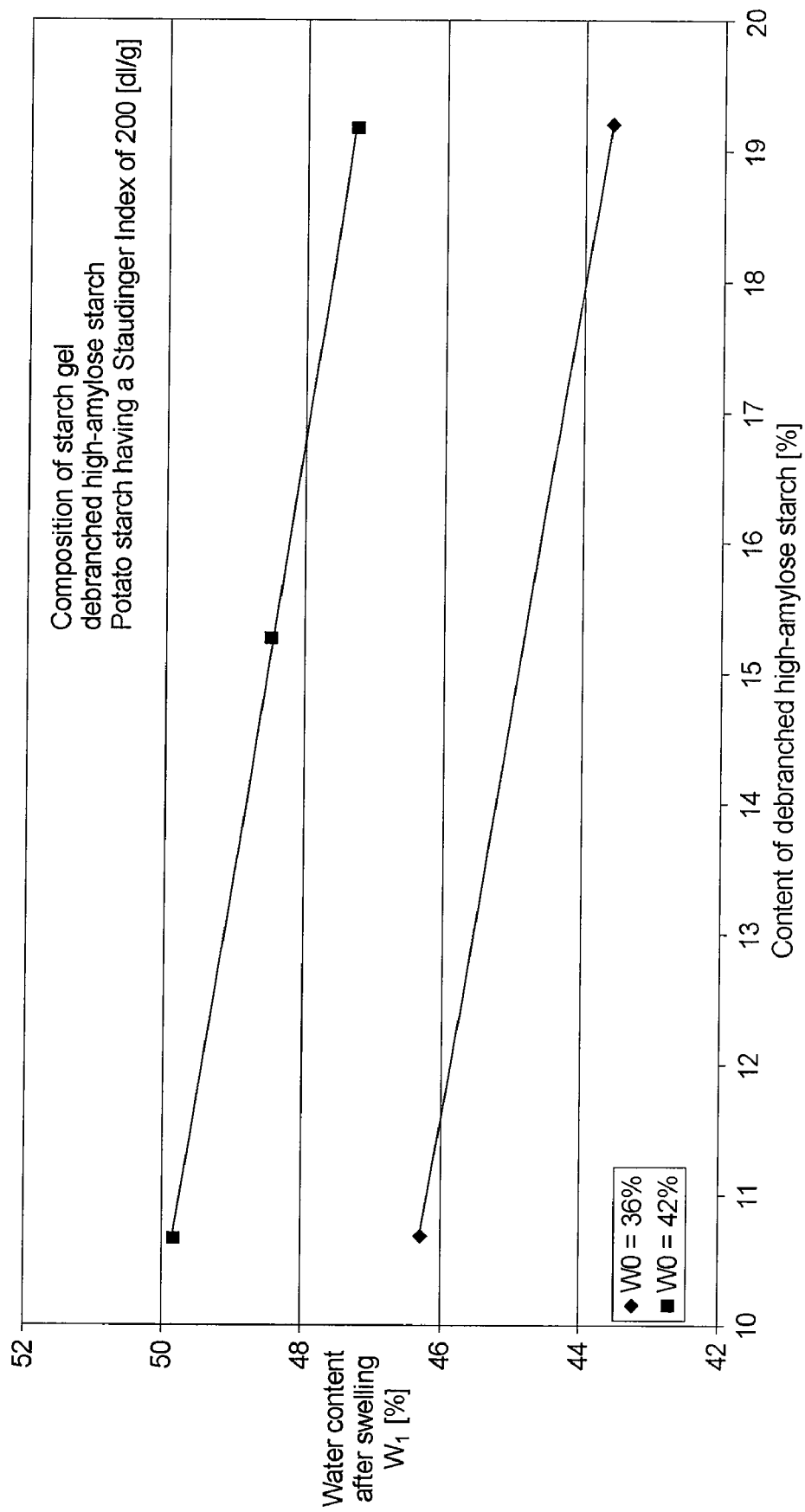
FIG. 2: shows the influence of the content of networking starch on the swelling

The measured values in FIG. 2 are based on the same procedure and measurement method as in FIG. 1 but in this case the content of networking starch is varied in order to study its influence. The results show that the water content after swelling decreases with increasing content of networking starch. The influence of the water content $W_0$ can also be seen.

Example 3

Figure 3:
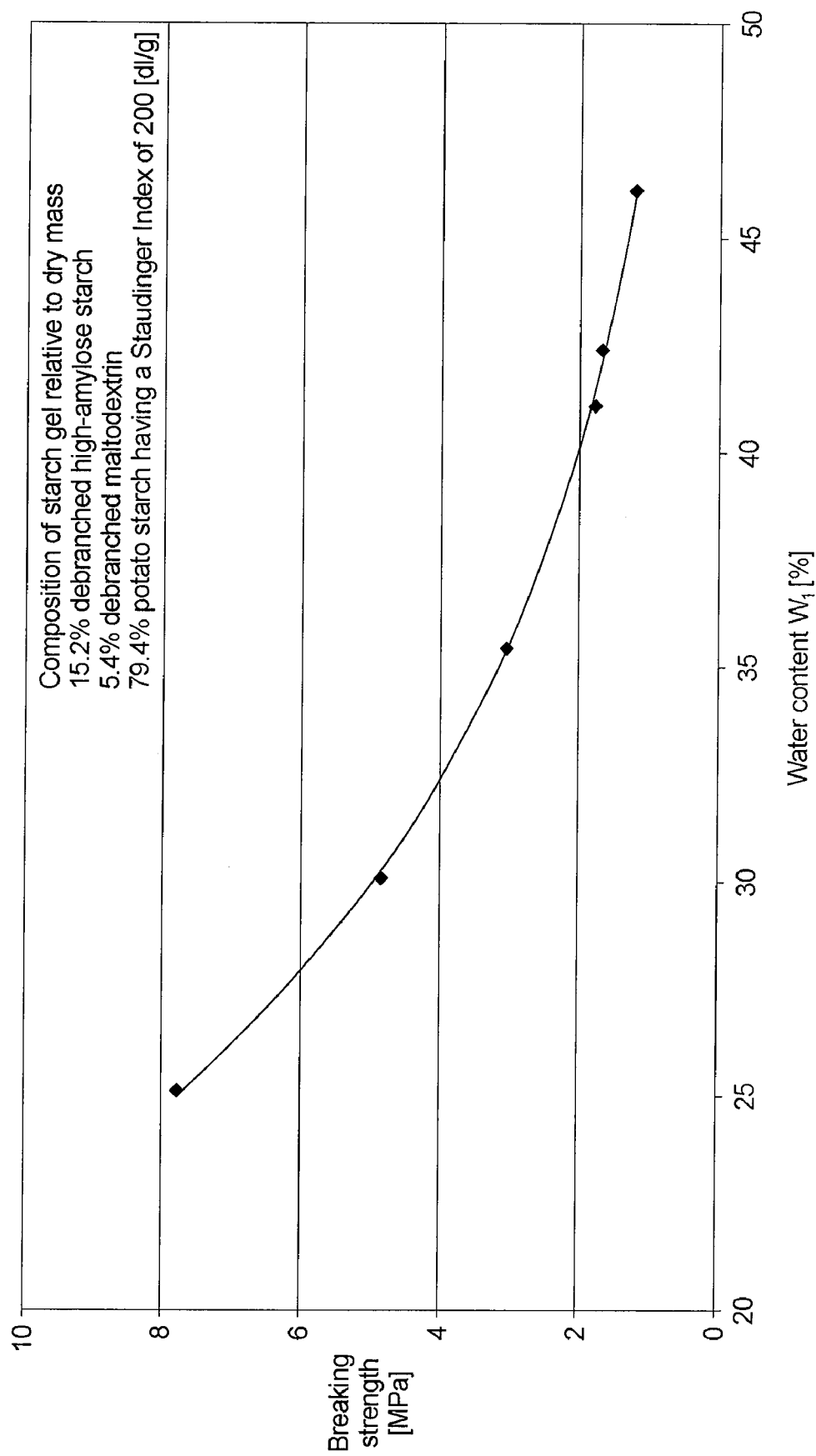
FIG. 3: shows the dependence of the tensile breaking strength on the water content of swollen starch gel

FIG. 3 shows the breaking strength of starch networks as a function of the water content $W_1$ (water content after swelling in water). Plasticised potato starch was used as the basic starch and a mixture of debranched maltodextrin and debranched high-amylose starch was used as the networking starch, wherein the components were dissolved and supercooled separately before being supplied together to the basic mixture. With decreasing water content $W_1$ of the swollen networks, the breaking strength increases significantly up to around 8 MPa at $W_1$=25%. This is an astonishing result which could be obtained by exhausting the possibilities of the method according to the invention. Conventional thermoplastic-starch-based materials have strengths in this range but they dissolve completely in water. With the starch networks according to the invention, it was now possible to obtain typical TPS strengths even after complete swelling in water. The advantages and possibilities of networks can be seen quite clearly here. The different degrees of swelling or water contents $W_1$ were obtained by varying the water content $W_0$ of the networks during and after the network formation. Low water contents $W_1$ were obtained by means of low water contents $W_0$.

Example 4

Starch networks according to the invention as described could be obtained by means of the proposed method by using basic starches which can form no gels or networks, with starches which do crystallise but by themselves form no gels, wherein heterocrystallisation of the components is decisive herefor. As an example of such a basic, non-gelatinisable starch, waxy maize in native form was mixed with 15% dissolved debranched maltodextrin and the mixture was plasticised at high shear velocities. The water content of the mixture W0 during and after network formation was 41%. After subsequent swelling of samples in the form of films in water, a water content $W_1$ of 49% was obtained. It could thus be shown that a network as present.

Example 5

Figure 4:
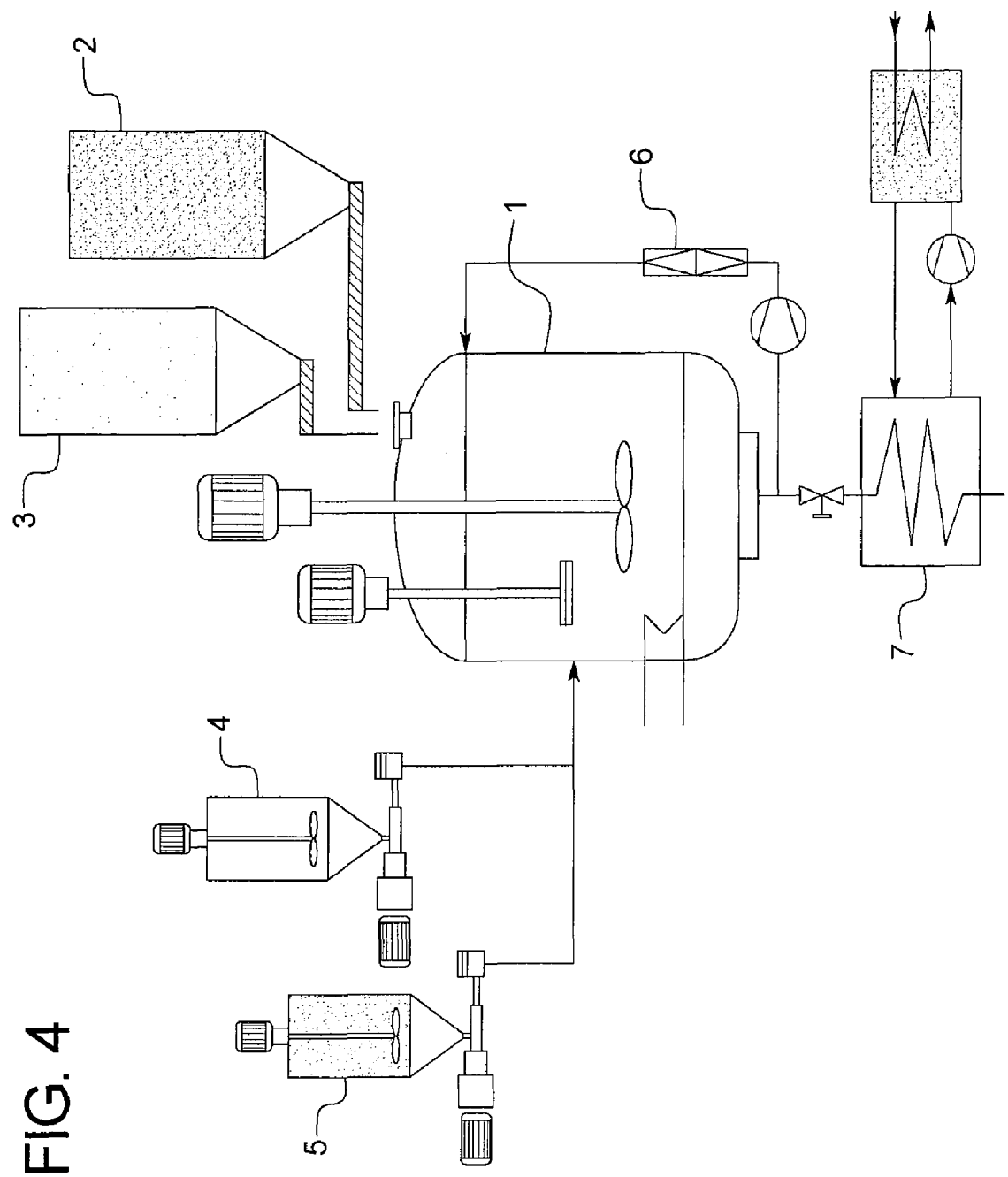
FIG. 4: shows an example for the preparation of solutions containing networking polysaccharides

FIG. 4 shows a schematic diagram of an example for the production of solutions of networking polysaccharides. In this case, two networking polysaccharides, for example, a debranched high-amylose starch 2) and a debranched maltodextrin 3) are metered into a mixing reactor 1) as well as two preliminarily tempered softeners 4) and 5). In addition, a nuclei stabiliser such a glycogen can also be metered in. The components are mixed and heated in the mixing reactor 1).

The mixing time and the temperature are determined according to the design and or type of plant and the required properties at the end product. For example, after a time of 1 min and at a temperature of 180° C., the mixture is dispersely mixed via a static mixer 6) by means of a pump. As a result of these measures, a solution of two networking polysaccharides is produced which can have different states according to time and temperature. The type and quality of the mixing material of the solution is determined according to the envisaged applications or requirements of the polysaccharide network to be produced. The prepared networking polysaccharide solution (third fluid) can then be cooled or supercooled for example, using a heat exchanger 7) and thus supplied to the following process step f) by means of a desired number of nuclei.

A single networking polysaccharide or more than two polysaccharides can be processed similarly. Alternatively, a plurality of networking polysaccharides can each be processed according to this method, brought together before the heat exchanger or after passing through the heat exchanger, each supplied singly to the first fluid in step f).

This process can be conducted continuously according to the type and/or design of the plant components and/or the driving method and/or the mixture ratios and/or the composition. In this case, after preparation via the static mixer the material flow is fed directly via the heat exchanger and prepared for the next step.

Example 6

Figure 5:
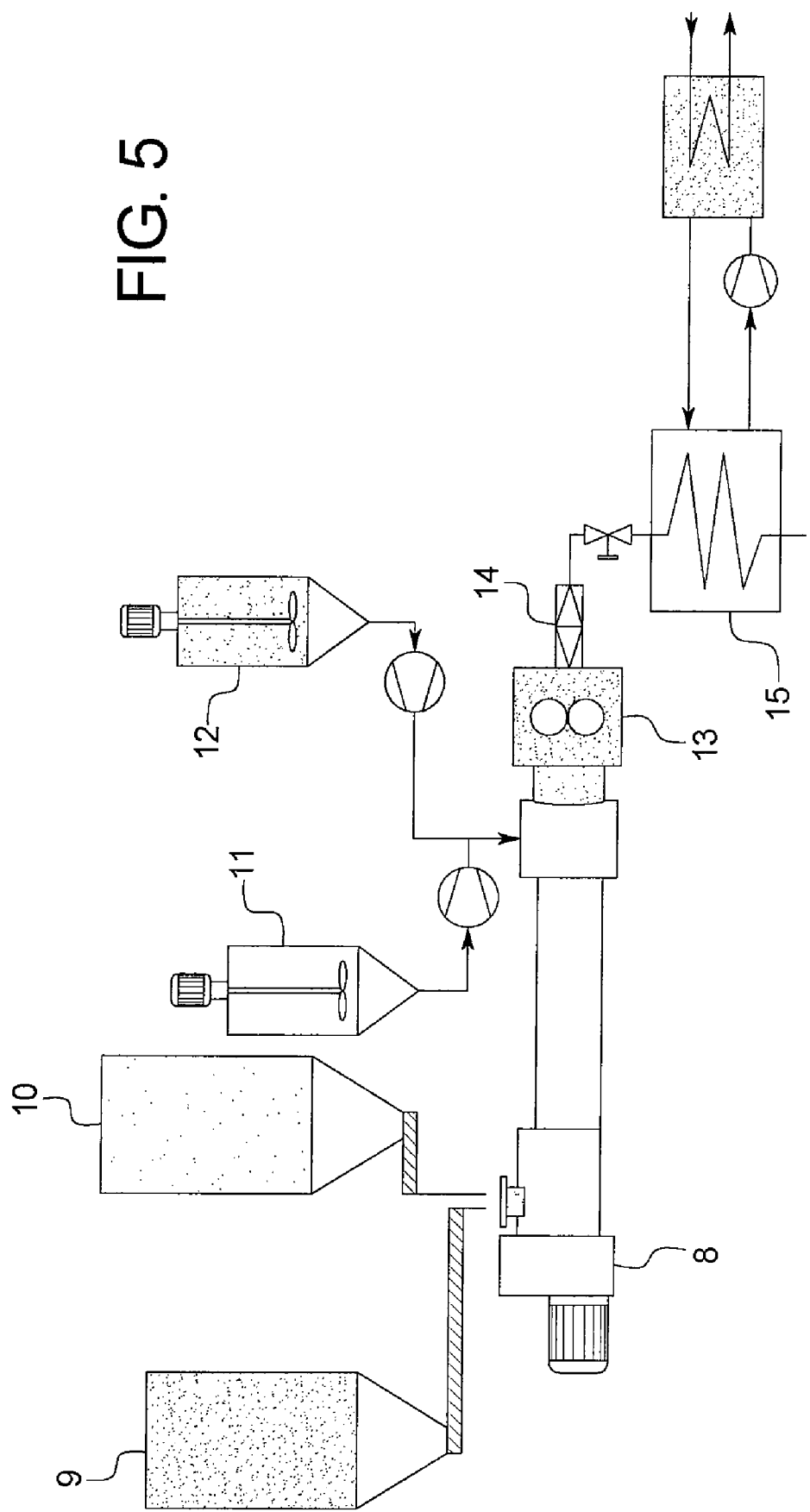
FIG. 5: shows an example for the continuous preparation of solutions containing networking polysaccharide

FIG. 5 shows an example for the continuous production of a networking polysaccharide solution. The networking polysaccharides 9) and 10) are metered continuously into the pump extruder 8). After a first conveying zone, the softeners 11) and 12) are also metered in continuously. The pump extruder supplies the components to a geared pump 13). The geared pump builds up the required pressure to pump the components via a static mixer 14) where, for example at 200° C. dispersive mixing takes place and the polysaccharides are dissolved within seconds under shearing. This solution is then cooled or supercooled in a controlled fashion via a heat exchanger 15) whereafter it can be supplied to process step f). By means of this variant of the method, especially high concentrations of networking polysaccharides can be transferred into solutions.

Similarly a plurality of networking polysaccharides can be processed jointly or alternatively respective polysaccharides can be processed singly in accordance with this method, brought together before or after the heat exchanger or supplied singly to process step f).

Example 7

Figure 6:
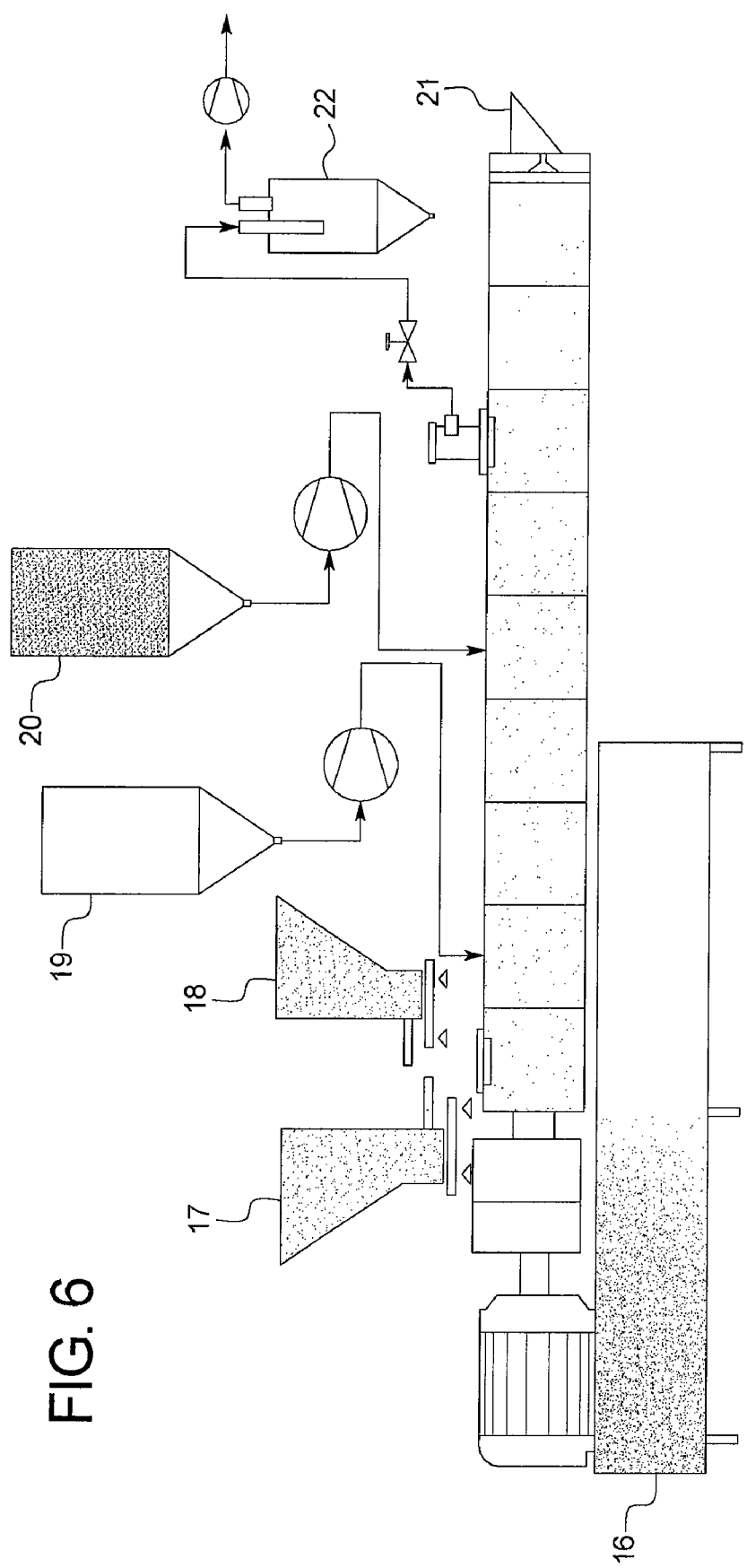
FIG. 6: shows an example for the production of polysaccharide networks

In accordance with FIG. 6, two basic polysaccharides 17) and 18) are metered continuously into a preparation extruder 16). After a short conveying distance, a softener 19) is metered in. The basic polysaccharides and the softener are prepared to give a first fluid using suitable screw geometry, rotation speed and temperature control. The networking polysaccharide solution 20) prepared for example in accordance with example 1 or 2 is then metered into the preparation extruder and then mixed with the first extruder. After mixing, softener fractions can be removed using outgassing technology 22). The required pressure is then built up to continuously form the mixture via a forming tool 21).

In order to obtain blends of polysaccharide network with polymers, after outgassing the polysaccharide mixture a plasticised polymer can be supplied for example via a side extruder and then mixed with this to form a blend. A foam can be obtained if a suitable propellant is added to the process.

Example 8

Figure 7:
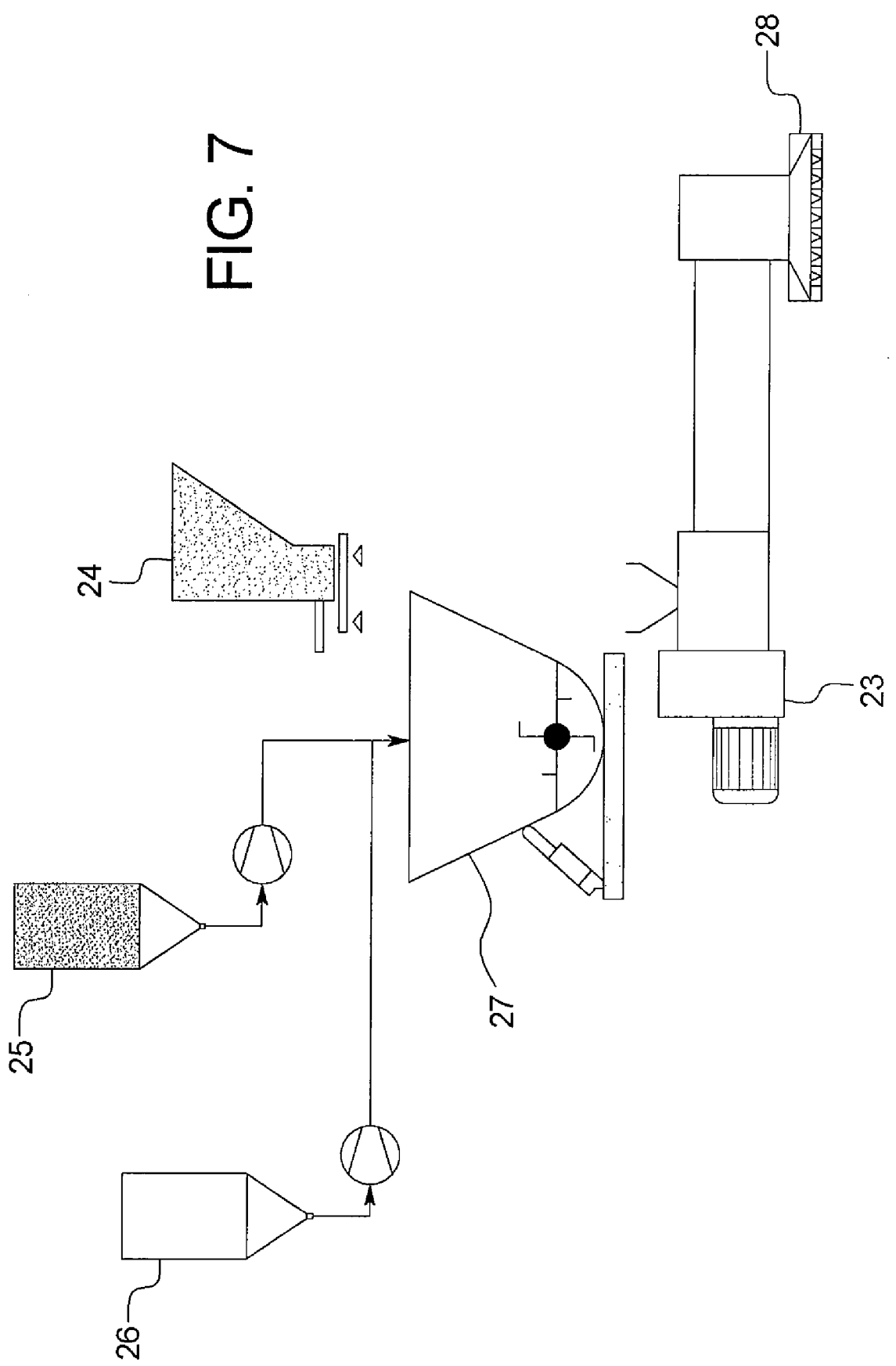
FIG. 7: shows an example for the production of polysaccharide networks

In FIG. 7 unlike in FIG. 6 the mixture is prepared in batches. A basic polysaccharide 24) and a softener 26) are metered into the mixture and mixed. The solution 25) containing the corresponding quantity of networking polysaccharide is also metered into the mixer and the total mixture is mixed. This total mixture is then brought into a desired form by means of a form extruder 23) and via a forming device 28).

REFERENCE LIST

1 Mixing reactor
2 Metering device for networking PS A
3 Metering device for networking PS B
4. Metering device for WM1
5 Metering device for WM2
6 Dispersing device
7 Heat exchanger
8 Pump extruder
9 Metering device for networking PS A
10 Metering device for networking PS B
11 Metering device for WM1
12 Metering device for WM2
13 Toothed gear pump
14 Static mixer
15 Heat exchanger device
16 Preparation extruder
17 Metering device for basic PS C
18 Metering device for basic PS D
19 Metering device for WM3
20 Metering device for networking PS solution
21 Forming device
22 Outgassing device
23 Forming extruder
24 Metering device for basic PS E
25 Metering device for networking PS solution
26 Metering device for WM3
27 Mixer
28 Forming device PS Polysaccharide
WM Softener It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A method for the production of a polysaccharide-based network, the method comprising:
   forming a polysaccharide-based network from a total mixture of components comprising at least one basic polysaccharide and at least one networking polysaccharide by one of homocrystallization and heterocrystallization, wherein the basic polysaccharide is plasticized, the networking polysaccharide is dissolved, and the components are mixed in a molecularly disperse fashion, wherein the method comprises the following steps in at least one process zone:
   a) supplying a basic polysaccharide;
   b) dissolving a networking polysaccharide to obtain a fluid by the action of a softener, wherein in step b) a softener content $WM_d$ of the networking polysaccharide is in the range 40-99 wt.-%, a pressure p is in the range of being identical to the water vapor pressure $p_W(T)$ at the respective temperature up to 100 $p_W(T)$, a duration $\Delta t_d$ of the dissolving is in the range 5 sec-7 min, and—provided that the networking polysaccharide is starch—a pH of the networking polysaccharide solution is in the range 5-12;
   c) incorporating the fluid from step b) to the basic polysaccharide from step a);
   d) combining the basic polysaccharide from step a) and the fluid from step b) into a total mixture, wherein the softener content $WM_2$ is less than 60% by weight, to form a polysaccharide network after steps a) to d) have been completed, wherein the basic polysaccharide is plasticized at the same time as the mixing to the total mixture takes place, wherein a shear velocity $G_d$ in the steps b) and c) is in the range from 10/s to 100,000/s.

2. The method according to claim 1, wherein the networking polysaccharide has a degree of branching $Q_b$ of less than 0.01.

3. The method according to claim 1, wherein the networking polysaccharide has an average degree of polymerisation DP of less than 100.

4. The method according to claim 1, wherein the basic polysaccharide is a basic starch and the networking polysaccharide is a networking starch.

5. The method according to claim 1, wherein in at least one of steps b) to d) a softener is removed at least partly actively from the method.

6. The method according to claim 1, wherein at least one polymer is supplied to the method in at least one of the following steps:
   step a);
   the incorporation of the fluid from step b) to the basic polysaccharide from step a);
   the combination of the basic polysaccharide and the fluid from step b) into a total mixture;
   after the combination of the basic polysaccharide and the fluid from step b) into a total mixture;
   before the formation of a polysaccharide network from the total mixture.

7. A method for the production of a polysaccharide-based network, the method comprising:

forming a polysaccharide-based network from a total mixture of components comprising at least one basic polysaccharide and at least one networking polysaccharide by one of homocrystallization and heterocrystallization, wherein the basic polysaccharide is plasticized, the networking polysaccharide is dissolved, and the components are mixed in a molecularly disperse fashion, wherein the method comprises the following steps in at least one process zone:

a) supplying a basic polysaccharide;
b) dissolving a networking polysaccharide to obtain a first fluid by the action of a softener, wherein in step b) the first fluid is overheated, a softener content $WM_d$ of the networking polysaccharide is in the range 40-99 wt.-%, a pressure p is in the range of being identical to the water vapor pressure $p_W(T)$ at the respective temperature up to 100 $p_W(T)$, a duration $\Delta t_d$ of the dissolving is in the range 5 sec-7 min, a heating rate $v_d$ is in the range 1-300° C./min, an overheating temperature $T_{LU}$ is in the range 80-260° C. and—provided that the networking polysaccharide is starch—a pH of the networking polysaccharide solution is in the range 5-12;
c) supercooling the first fluid to obtain a second fluid, wherein the softener content $WM_d$ of the networking polysaccharide is in the range 40-99 wt.-%, a pressure p is in the range of being identical to a water vapor pressure $p_W(T)$ at the respective temperature up to 100 $p_W(T)$, a duration $\Delta t_e$ of the supercooling is in the range 5 sec-7 min, a cooling rate $v_e$ is in the range 5-300° C./min, a temperature $T_{L1}$ is in the range 0° C. to 0.9 $T_{LU}$ and—provided that the networking polysaccharide is starch—a pH of the networking polysaccharide solution is in the range 5-12;
d) incorporating the second fluid from step c) to the basic polysaccharide from step a);
e) combining the basic polysaccharide from step a) and the fluid from step c) into a total mixture, wherein the softener content $WM_2$ is less than 60% by weight, to form a polysaccharide network after steps a) to e) have been completed, wherein the basic polysaccharide is plasticized at the same time as the mixing to the total mixture takes place, wherein a shear velocity $G_d$ in the steps b) and/or c) and d) is in the range from 10/s to 100,000/s.

8. The method according to claim 7, wherein the networking polysaccharide has a degree of branching $Q_b$ of less than 0.01.

9. The method according to claim 7, wherein the networking polysaccharide has an average degree of polymerisation DP of less than 100.

10. The method according to claim 7, wherein the basic polysaccharide is a basic starch and the networking polysaccharide is a networking starch.

11. The method according to claim 7, wherein in at least one of steps b) to e) a softener is removed at least partly actively from the method.

12. The method according to claim 7, wherein in step c) shortly before step d) the second fluid containing networking polysaccharide is treated with ultrasound.

13. The method according to claim 7, wherein at least one polymer is supplied to the method in at least one of the following steps:

step a);
the incorporation of the second fluid from step c) to the basic polysaccharide from step a);
the combination of the basic polysaccharide and the second fluid from step c) into a total mixture;
after the combination of the basic polysaccharide and the second fluid from step c) into a total mixture;
before the formation of a polysaccharide network from the total mixture.

* * * * *